(12) United States Patent
Ueno et al.

(10) Patent No.: US 6,548,703 B1
(45) Date of Patent: *Apr. 15, 2003

(54) TONING AGENT

(75) Inventors: Ryuzo Ueno, Nishinomiya (JP);
Masaya Kitayama, Takarazuka (JP);
Kenji Minami, Sennan (JP);
Masamitsu Kubotsu, Nishinomiya (JP)

(73) Assignee: Kabushiki Kaisha Ueno Seiyaku Oyo Kenkyujo, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/581,743

(22) PCT Filed: Oct. 14, 1999

(86) PCT No.: PCT/JP99/05657

§ 371 (c)(1),
(2), (4) Date: Jun. 16, 2000

(87) PCT Pub. No.: WO00/23526

PCT Pub. Date: Apr. 27, 2000

(30) Foreign Application Priority Data

Oct. 16, 1998 (JP) .......................................... 10-295200

(51) Int. Cl.⁷ .......................... C07C 233/05; G03G 9/00

(52) U.S. Cl. ...................... 564/158; 564/153; 562/467; 560/56; 430/105; 534/841; 534/842

(58) Field of Search ................................. 564/158, 153; 562/467; 560/56; 430/105; 534/841, 842

(56) References Cited

U.S. PATENT DOCUMENTS

| 4,224,221 A | 9/1980 | Burley et al. |
| 4,530,724 A | 7/1985 | Ueno et al. |
| 4,655,844 A | 4/1987 | Ueno et al. |
| 5,847,233 A | * 12/1998 | Ueno et al. ............... 568/735 |

FOREIGN PATENT DOCUMENTS

| JP | 56-116753 | 9/1981 |
| JP | 58-42662 | 3/1983 |
| JP | 61-181864 | 8/1986 |
| JP | 62-138560 | 6/1987 |
| JP | 2-302471 | 12/1990 |
| JP | 7-238231 | 9/1995 |
| WO | 9632366 | * 10/1996 |

* cited by examiner

Primary Examiner—Shailendra Kumar
(74) Attorney, Agent, or Firm—Sughrue Mion, PLLC

(57) ABSTRACT

A toning agent for an azo pigment, an azo pigment with a modified tone, and process for preparing the same are provide. 2-hydroxynaphthalene-3,6-dicarboxylic acid or a derivative thereof is admixed with a primary coupler component for an azo pigment and the mixed coupler composition and an aromatic diazonium are coupled.

6 Claims, 1 Drawing Sheet

TONING AGENT

This application is a 371 of PCT/JP99/05657, filed Oct. 14, 1999.

TECHNICAL FIELD

The present invention relates to a novel toning agent comprising 2-hydroxynaphthalene-3,6-dicarboxylic acid and derivatives thereof. In more detail, the present invention relates to a toning agent for an azo pigment and a method for preparing an azo pigment with a modified tone.

BACKGROUND ART

Azo pigments are synthesized by coupling a diazonium salt with a coupler. Among the couplers employed in the coupling reaction, hydroxynaphthalene-mono-carboxylic acids and derivatives thereof are especially important compounds.

Hydroxynaphthalene mono carboxylic acids used as couplers include 2-hydroxynaphthalene-3-carboxylic acid, 2-hydroxynaphthalene-6-carboxylic acid and the like and 2-hydroxynaphthalene-3-carboxylic acid is popular.

Azo compounds synthesized with the coupler component of 2-hydroxynaphthalene-3-carboxylic acid include Brilliant Carmine 6B (Pigment Red 57) and Watchung Red (Pigment Red 48). They are prepared by diazotizing 6-amino-m-toluensulfonic acid and 6-amino-4-chloro-m-tolunensulfonic acid, respectively, and coupling the resulting diazonium salts with 2-hydroxynaphthalene-3-carboxylic acid.

In addition, an azo pigment which incorporate 2-hydroxynaphthalene-6-carboxylic acid as a coupler component has also been known (Japanese Patent Application Laid Open Nos. 302471/90 and 238231/95).

The azo pigments have been applied to various purposes, for example, printing ink, coating composition, paint composition, plastics and cosmetics. Depending on the application, a variety of performances are required for the pigment. For example, brightness and transparency are required for printing ink, durability and hiding effect are required for coating composition, and thermal resistance is required for plastics. In formulating even pigments comprising a compound having the same chemical structure, therefore, it may be necessary to formulate such pigments exhibiting properties or characteristics, which fit well with their intended application fields.

The color and other properties of a pigment are in principle the attributes of its chemical structure, but its characteristics, such as brilliance, transparency and hiding power, may change as well depending upon the physical parameters of the pigment, such as fineness, shape and surface conditions of the particles. The property of pigments can be altered to some extent by modifying the manufacturing steps, or utilizing such additives as wood rosin, for example, but cannot to a satisfactory degree. On the other hand, it is also known that the tone and physical properties of pigments can be modified by replacing a part of 2-hydroxynaphthalene-3-carboxylic acid, which is used as a coupling component, with a suitable amount of a toning agent (Japanese Patent Laid-Open No. 116753/1981). The present applicant disclosed several compounds which can modify the tone of an azo pigment (Japanese Patent Laid-Open Nos. 42662/1983, 181864/1986, 138560/1987 and 138561/1987).

SUMMARY OF THE INVENTION

Objects of the present invention are to provide a toning agent which enable to modify the tone of an azo pigment as desired, and also to provide a process for preparing an azo pigment with the modified tone.

The inventors studied intensively on toning agents which enable to modify the tone of an azo pigment as desired, and found that it could be modified by admixing 2-hydroxynaphthalene-3,6-dicarboxylic acid or a derivative thereof with the primary coupler component of the azo pigment.

Accordingly, the present invention provides a toning agent comprising a compound having the general formula [I];

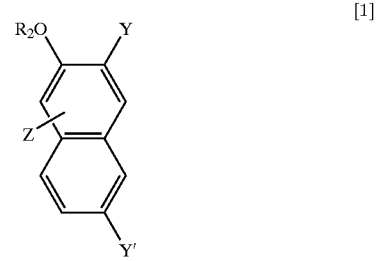

wherein

Y is —(CONH)n-X or —COR,

Y' is —(CONH)n-X' or —COR',

X and X' are optionally branched alkyl groups having 1–20 carbon atoms, optionally substituted aromatic groups, or optionally substituted heterocyclic groups having conjugated double bonds, n is an integer of 1 or 2, R and R' are hydroxy groups, optionally branched alkoxy groups having 1–6 carbon atoms, benzyloxy groups, phenyloxy groups or phenacyloxy groups, provided that when either R or R' is a hydroxy group, said group may optionally form an acceptable salt, $R_2$ is a hydrogen atom, an optionally branched alkyl group having 1–6 carbon atoms, an acyl group having 1–6 carbon atoms or a phenyl alkyl group, Z is one or more atoms or groups selected from the group consisting of a hydrogen atom, an optionally branched alkyl group having 1–6 carbon atoms, an optionally branched alkoxy group having 1–6 carbon atoms, a halogen atom, a sulfo group, a nitro group, a nitroso group, and an amino group, provided that Z may be combined with either of the two rings of the naphthalene ring.

Further, the present invention also provide a process for preparing an azo pigment comprising the steps of admixing the toning agent represented by the above formula [I] with the primary coupler component for the azo pigment and, coupling the mixed coupler composition with a diazonium salt of an aromatic compound.

The term "toning" or "tone" as used in this invention denotes to provide pigments, by some means, with controlled properties or characteristics in terms of, for example, color, brilliance, transparency and hiding power.

The term "toning agent" as used in this invention, denotes a part of coupler composition used in preparing an azo pigment. A small amount of the toning agent may be admixed with a primary coupler component used in preparation of the azo pigment to provide the pigment with a modified tone than that obtained without the toning agent. Generally, the amount of the toning agent contained in the whole coupler composition used for preparing the desired azo pigment may be less than 50 mol %, preferably less than 10 mol %, and especially, less than 5 mol %. When said amount of the toning agent is admixed with the primary coupler component, an azo pigment with a modified tone, which is different from those obtained by mixing two azo pigments, each of which is obtained by means of respective couplers (i.e. the primary coupler and the toning agent) in the ratio of the amount of the respective couplers, can be obtained.

As described above, the toning agent used in this invention, i.e. the compound represented by the general formula [I], is a 2-hydroxynaphthalene-3,6-dicarboxylic acid, or ester, amide or ureide derivative thereof.

In the present invention, the amide or ureide derivative may be prepared by obtaining acid chloride of the starting compound by means of thionyl chloride or the like in a solvent such as xylene or sulfolane in a conventional manner, and then reacting the acid chloride with amine or urea. Alternatively, they can be prepared by reacting the starting compound directly with amine or urea in the presence of phosphorous trichloride, dicyclohexylcarbodiimide or the like.

Examples of the amines or ureas, i.e. starting materials which constitutes the group X or X' in the Y and Y' may include optionally branched alkyl groups having 1–20 carbon atoms, optionally substituted aromatic amino compounds such as aniline (X or X' is a phenyl group), amino naphthalene (X or X' is a naphthyl group), aminoanthracene (X or X' is a anthryl group), aminopyrene (X or X' is a pyrenyl group), amino fluorene (X or X' is a fluororenyl group) or aminoanthraquinone (X or X' is an anthraquinonyl group); and optionally substituted heterocyclic compounds having conjugated double bonds such as aminobenzimidazolone (X or X' is a benzimidazolonyl group), aminocarbazole (X or X' is a carbazolyl group), aminopyridine (X or X' is a pyridyl group), aminothiazole (X or X is a thiazolyl group), aminobenzothiazole (X or X' is a benzothiazolyl group), or aminoimidazole (X or X' is an imidazolyl group) as well as aminoindole (X or X' is an indolyl group), aminothiophene (X or X' is a thiofuryl group), aminophenothiazine (X or X' is a phenothiazinyl group), aminoacridine (X or X' is an acridinyl group), and aminoquinoline (X or X' is a quinolinyl group). Examples of the substituents include halogen atom, nitro group, lower alkyl group, lower alkoxy group, cyano group, phenyl group, morpholino group, phenoxy group, sulfo group, carboxyl group, amide group (for example, phenylaminocarbonyl group) and the like, and the phenoxy and amide groups may also have another substituent such as halogen atom, lower alkyl group, lower alkoxy group, alkylaminosulfonyl group, nitrile group or the like.

By reacting the above described amino compound and potassium cyanate, a corresponding urea can be obtained. That is, phenyl urea, for example, can be obtained from aniline.

Y or Y' may represent —COR or —COR'. When either R or R' is a hydroxy group, it may form an alkaline metal salt. Examples of the alkaline metals include sodium, potassium, lithium and the like. When R is —OR$_1$ or R' is —OR$_1$', R$_1$ or R$_1$' is an optionally branched alkyl group having 1–6, preferably 1–4 carbon atoms, a phenyl group, a benzyl group, or a phenacyl group, each of the groups may be substituted.

Preferably, at least one of Y and Y' is carboxylic acid (—COOH).

R$_2$ is a hydrogen atom, an optionally branched alkyl group having 1–6, preferably 1–4 carbon atoms, especially, methyl or ethyl group; an acyl group having 1–6, preferably 1–4 carbon atoms, especially acetyl group; or a phenylalkyl group wherein the phenylalkyl group may have a substituent such as a halogen atom or a lower alkyl group.

The compound of the formula [I] used as a toning agent of the present invention may be prepared in a manner described in WO96/32366 and WO98/16513.

The process of the present invention for preparing an azo pigment with a modified tone may be conducted by admixing the toning agent of the formula [1] with the primary coupler component for the azo pigment, and coupling the obtained mixed coupler composition with a diazonium salt of an aromatic compound, which is obtained by diazotizing an aromatic amine.

Examples of the aromatic amines include aniline, monoamino condensed polycyclic hydrocarbons such as naphthylamine, monoaminoanthracene, monoaminoindene, and monoaminofluorenone, as well as monoaminoindole, monoaminobenzothiophene, monoaminoquinoline, and monoaminocarbazole. The above-described aromatic amines may have a substituent. Examples of the substituents include halogen atom, lower alkyl group, especially methyl, halogenated lower alkyl group, cyano group, nitro group, lower alkoxy group, amide group, sulfo group, alkylamino sulfonyl group, aminocarbonyl group, phenylaminocarbonyl group, phenoxy group, alkoxycarbonyl group, hydroxy group, benzoylamino group, toluidylamino group, triazylamino group, and pyrimidylamino group.

The azo pigment obtained by the present invention may be used for preparing a lake pigment. Agents which is used to make the lake pigment may include Ca salt, Ba salt, Sr salt and Mn salt. The lake pigment may be prepared in a conventional manner.

The amount of the compound of formula [I] in the coupler composition is not limited. However, too much toning agent will provide a color completely different from the original color of the pigment, and therefore, the amount of the toning agent in the whole coupling composition may generally be less than 50 mol %, preferably, 0.1–10 mol %, especially, 0.2–5.0 mol %.

The primary coupler component of the present invention may be any as far as different from the compound represented by the formula [I]. Examples of the coupler component include naphthols such as α-naphthol and β-naphthol, hydroxynaphthalene monocarboxylic acids or derivatives thereof. Preferable couplers are hydroxynaphthalene monocarboxylic acids and derivatives thereof, for example, 2-hydroxynaphthalene-3-carboxylic acid, 2-hydroxynaphthalene-6-carboxylic acid, or esters or amides thereof.

Examples of the esters include alkyl esters such as methyl, ethyl, and propyl, phenyl ester, benzyl ester, phenacyl ester and the like and each of the ester groups may have a substituent.

Examples of the amides include aromatic amide which may optionally form a heterocyclic group, such as phenylamide, α- or β-napthylamide, anthraquinonylamide, benzimidazolonylamide, carbazolylamide, pyridylamide, thiazolylamide, benzothiazolylamide, imidazolylamide, indolylamide, thiofurylamide, phenothiazinylamide, acridinyl amide and quinolinylamide. Each of these amide groups may have a substituent, for example, halogen atom, nitro group, lower alkyl group, lower alkoxy group, cyano group, phenoxy group, amino group such as methylcarbonylamino group.

The process for preparing a diazonium salt from an amine is not limited. A conventional method comprising the step of diazotizing an amine with sodium nitrite may be employed.

According to the present invention, by admixing one or more compounds of the formula [I] with the primary coupler component, the crystal growth of the azo pigment synthesized with the mixed coupler composition is effected to provide a modified pigment with a modified color, tone and/or transparency.

The toning effects may vary widely depending on the kind of the diazonium compound used, or with the kind and amount of the compound of the formula [I] used.

Figure 1:
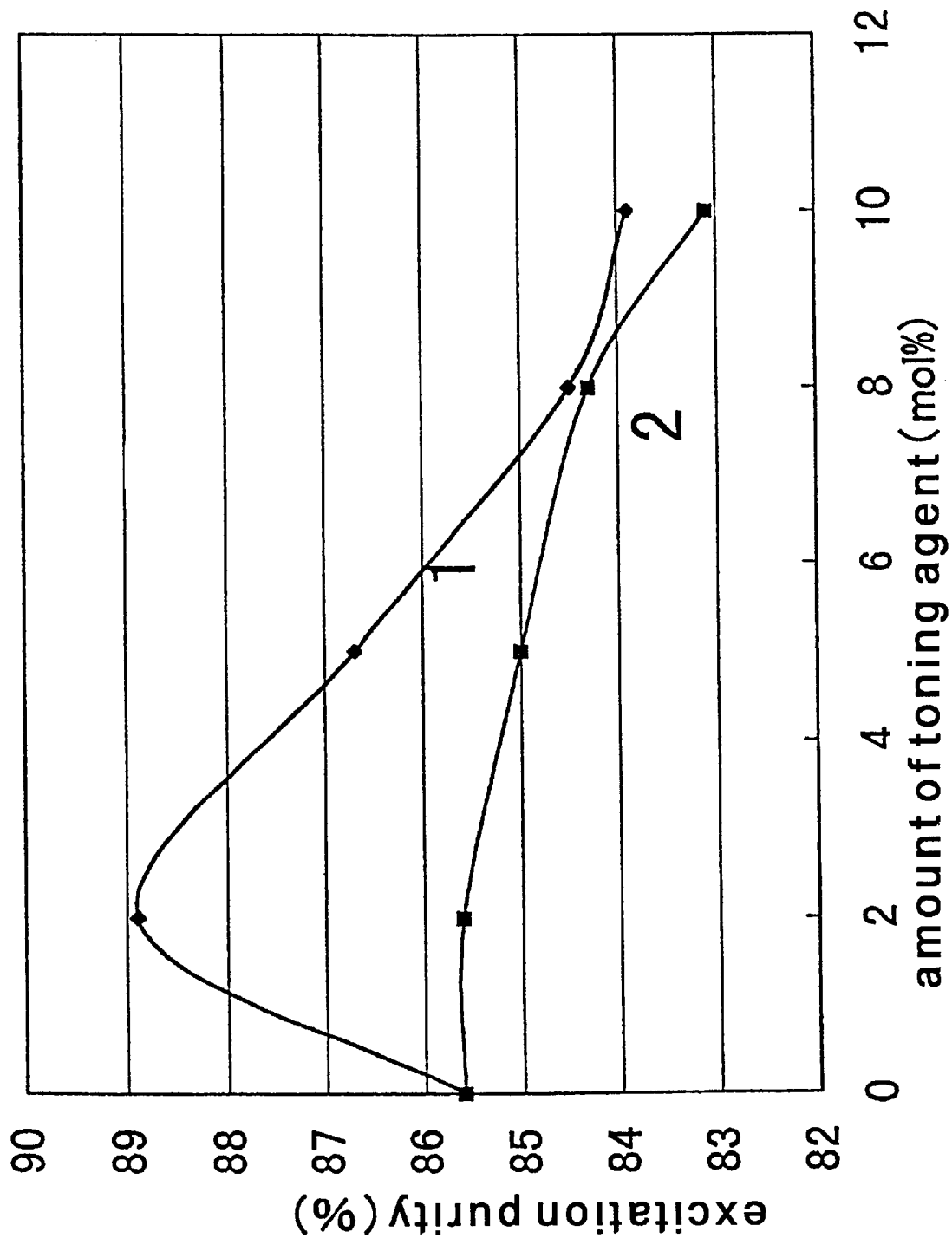
FIG. 1 represents a graph showing the relationship between the amount of the toning agent (mol %) and excitation purity of the obtained pigment (%) in respect of the red pigments obtained in Examples 1 and 18–20, and in Comparative examples 1–4.

DESCRIPTION OF THE SYMBOLS 1 represents excitation purity of the pigment obtained in Examples 1, 18–20. 2 represents excitation purity of the pigment obtained in Comparative examples 1–4.

The present invention will be further illustrated by the following examples.

EXAMPLE 1

4-aminotoluene-3-sulfonic acid (4B-Acid) (10.0 g) was dispersed in 400.0 g of water and added with 10.8 g of 35% aqueous hydrochloride. The obtained dispersion was warmed to 40° C., stirred for 30 minutes, and then cooled to 0–2° C. Then, 4.2 g of sodium nitrite solution in 20.0 g of water was added to the mixture and diazotized. Separately, 10.2 g of 2-hydroxynaphthalene-3-carboxylic acid, which was used as the primary coupler component, and 0.3 g of 2-hydroxy-3-methoxycarbonyl-6-carboxynaphthalene:

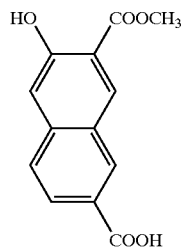

which was used as the toning agent, were dissolved into a mixed solution consisting of 800.0 g of water and 77.0 g of 10% aqueous sodium hydroxide, then added with 48.0 g of 5% aqueous rosin solution and kept at 10–15° C. The above obtained diazotized solution (445.0 g) was added dropwise to thus obtained solution over 30 minutes and conducted coupling reaction for 1 hour, and then the pH of the solution was adjusted to 9.0–9.5 with 10% aqueous hydrochloride. Then, 11.8 g of calcium chloride dehydrate in 70.0 g of water was added dropwise to the solution while maintaining it at 13±2° C. to provide lake compound and followed by 1 hour stirring. The pH of the obtained mixture was further adjusted to 6.0–6.5 with 10% aqueous hydrochloride, and the mixture was warmed to 70° C. and kept there for 10 minutes. After that, 200 g of water was added and the mixture was cooled gradually to 50° C. The product was obtained by filtration, washed with water, dried at 80° C. for one night to give 22.5 g of red pigment.

EXAMPLE 2

According to the same manner as described in Example 1 with the exception that 0.3 g of 2-hydroxy-3-hydroxycarbonyl-6-methoxycarbonyl naphthalene:

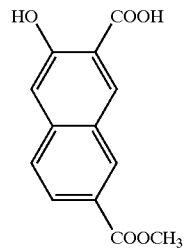

was used as the toning agent, 21.4 g of red pigment was obtained.

EXAMPLE 3

According to the same manner as described in Example 1 with the exception that 0.3 g of 2-hydroxy-3-hydroxycarbonyl-6-phenylaminocarbonyl naphthalene:

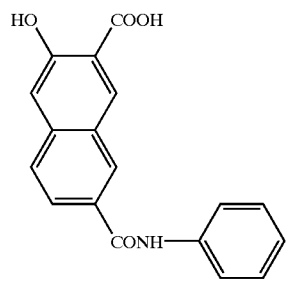

was used as the toning agent, 20.2 g of red pigment was obtained.

EXAMPLE 4

According to the same manner as described in Example 1 with the exception that 0.3 g of 2-hydroxynaphthalene-3,6-dicarboxylic acid:

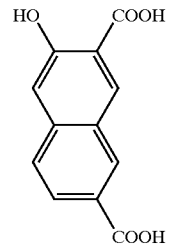

was used as the toning agent, 23.4 g of red pigment was obtained.

EXAMPLE 5

According to the same manner as described in Example 1 with the exception that 0.3 g of 2-hydroxy-3-phenylaminocarbonyl-6-carboxynaphthalene:

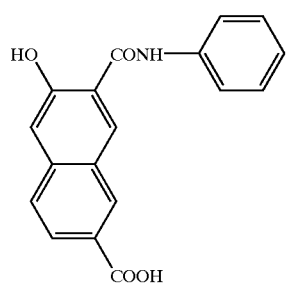

was used as the toning agent, 20.2 g of red pigment was obtained.

Synthesis Example 1

Synthesis of 2-hydroxy-3-naphthylaminocarbonyl-6-n-octyl aminocarbonylnaphthalene

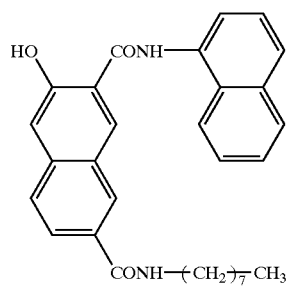

A dispersion of 7.1 g of 2-hydroxy-3-naphthylamino carbonyl-6-chlorocarbonylnaphthalene in 20 g of dry tetrahydrofuran was added with 5.2 g of n-octylamine dissolved in dry tetrahydrofuran and reacted under reflux for 12 hours. To the reaction mixture, 30 g of water was added and the precipitates were collected by filtration, washed with water and thus obtained crystal was washed with 30 g of methanol under reflux. The obtained mixture was cooled to 30° C. and filtrated, washed with methanol and dried to provide 4.8 of 2-hydroxy-3-naphthylaminocarbonyl-6-n-octyl aminocarbonylnaphthalene (decomposition point: 342.1° C.).

EXAMPLE 6

According to the same manner as described in Example 1 with the exception that 0.5 g of 2-hydroxy-3-naphthylaminocarbonyl-6-n-octylaminocarbonylnaphthalene obtained in the synthesis example 1 was used instead of the toning agent used in Example 1, 21.0 g of red pigment was obtained.

Synthesis Example 2

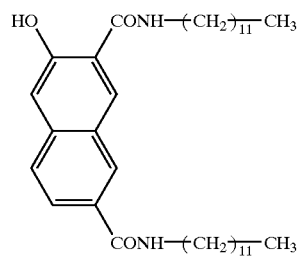

Synthesis of 2-hydroxy-3,6-di-n-dodecylaminocarbonyl naphthalene

A dispersion of 5.4 g of 2-hydroxy-3,6-dichloro carbonylnaphthalene in 20.0 g of dry tetrahydrofuran was added with 14.8 g of n-dodecylamine solution in 30 g of dry tetrahydrofuran and reacted under reflux for 12 hours. To the reaction mixture, 50 g of water was added and the precipitates were collected by filtration, washed with water and thus obtained crystal was washed with 30 g of methanol under reflux. The obtained mixture was cooled to 30° C. and filtrated, washed with methanol and dried to provide 3.3 g of 2-hydroxy-3,6-di-n-dodecylaminocarbonylnaphthalene (decomposition point: 382.9° C.).

EXAMPLE 7

According to the same manner as described in Example 1 with the exception that 0.6 g of 2-hydroxy-3,6-di-n-dodecylaminocarbonylnaphthalene obtained in the synthesis example 2 was used instead of the toning agent used in Example 1, 20.1 g of red pigment was obtained.

EXAMPLE 8

According to the same manner as described in Example 1 with the exception that 0.3 g of 2-hydroxy-3,6-dimethoxycarbonylnaphthalene:

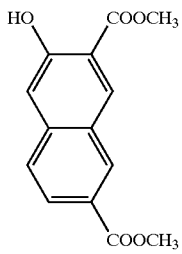

was used instead of the toning agent used in Example 1, 22.1 g of red pigment was obtained.

Synthesis Example 3

Synthesis of 2-hydroxy-3-phenylaminocarbonyl-6-n-hexa decylamino carbonylnaphthalene

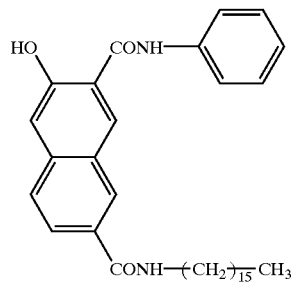

A dispersion of 6.5 g of 2-hydroxy-3-phenylaminocarbonyl-6-chlorocarbonylnaphthalene in 20.0 g of dry tetrahydrofuran was added with 9.2 g of n-hexadecylamine solution in 30 g of dry tetrahydrofuran and reacted under reflux for 12 hours. To the reaction mixture, 30 g of water was added and the precipitates were collected by filtration, washed with water and thus obtained crystal was washed with 30 g of methanol under reflux. The obtained mixture was cooled to 30° C. and filtrated, washed with methanol and dried to provide 3.8 g of 2-hydroxy-3-phenylaminocarbonyl-6-n-hexadecylaminocarbonyl naphthalene (decomposition point: 257.2° C.).

EXAMPLE 9

According to the same manner as described in Example 1 with the exception that 0.6 g of 2-hydroxy-3-phenylaminocarbonyl-6-n-hexadecylaminocarbonyl naphthalene obtained in the synthesis example 3 was used instead of the toning agent used in Example 1, 17.7 g of red pigment was obtained.

EXAMPLE 10

According to the same manner as described in Example 1 with the exception that 0.5 g of 2-hydroxy-3,6-di(2',4'-dimethylphenylaminocarbonyl)naphthalene:

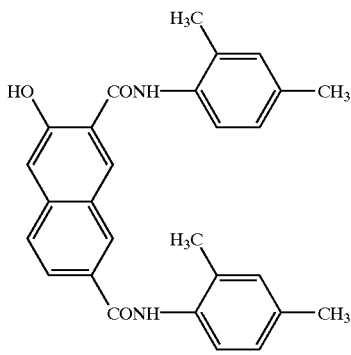

was used instead of the toning agent used in Example 1, 21.5 g of red pigment was obtained.

EXAMPLE 11

According to the same manner as described in Example 1 with the exception that 0.4 g of 2-hydroxy-3,6-diphenylaminocarbonylnaphthalene:

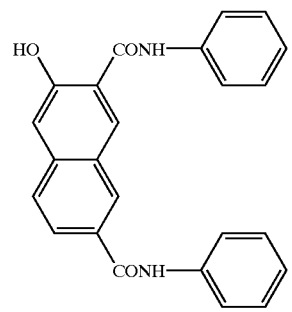

was used instead of the toning agent used in Example 1, 20.6 g of red pigment was obtained.

EXAMPLE 12

According to the same manner as described in Example 1 with the exception that 0.5 g of 2-hydroxy-3,6-di(2'-chlorophenylaminocarbonyl)naphthalene:

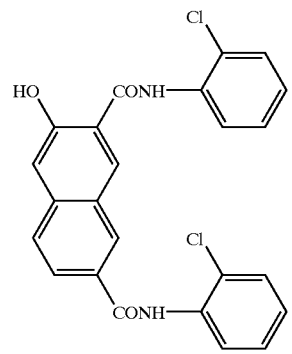

was used instead of the toning agent used in Example 1, 20.8 g of red pigment was obtained.

EXAMPLE 13

According to the same manner as described in Example 1 with the exception that 0.6 g of 2-hydroxy-3,6-diphenyletherphenylaminocarbonylnaphthalene:

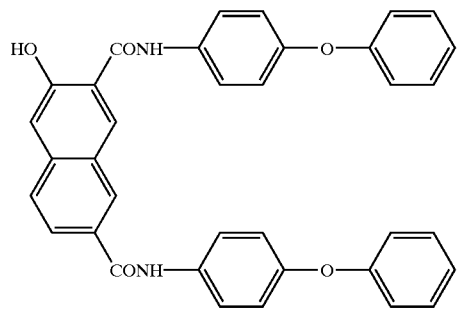

was used instead of the toning agent used in Example 1 18.9 g of red pigment was obtained.

EXAMPLE 14

According to the same manner as described in Example 1 with the exception that 0.4 g of 2-hydroxy-3,6-di-(2-pyridylaminocarbonyl)naphthalene:

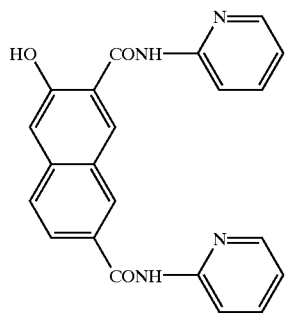

was used instead of the toning agent used in Example 1, 20.1 g of red pigment was obtained.

EXAMPLE 15

According to the same manner as described in Example 1 with the exception that 0.58 g of 2-hydroxy-3-(2',4'-dimethoxy)phenylaminocarbonyl-6-n-dodecylamino carbonylnaphthalene:

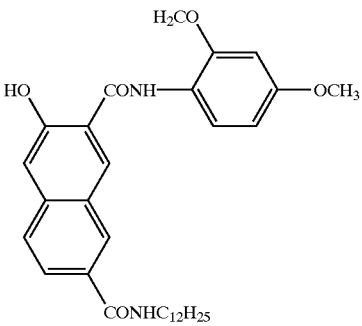

was used instead of the toning agent used in Example 1, 21.0 g of red pigment was obtained.

EXAMPLE 16

According to the same manner as described in Example 1 with the exception that 2-hydroxynaphthalene-6-carboxylic acid was used as the primary coupler instead of 2-hydroxynaphthalene-3-carboxylic acid used in Example 1, 21.5 g of red pigment was obtained.

EXAMPLE 17

According to the same manner as described in Example 1 with the exception that 2-hydroxynaphthalene-6-carboxylic acid was used as the primary coupler instead of 2-hydroxynaphthalene-3-carboxylic acid used in Example 1, and the toning agent was replaced with 0.3 g of 2-hydroxy-3-carboxy-6-methoxycarbonylnaphthalene, 22.8 g of red pigment was obtained.

Reference Example 1

According to the same manner as described in Example 1, with the exception that no toning agent was added and the amount of 2-hydroxynaphthalene-3-carboxylic acid was changed to 10.4 g, 23.4 g of red pigment was obtained.

Reference Example 2

According to the same manner as described in Example 1, with the exception that 1 0.4 g of 2-hydroxynaphthalene-6-carboxylic acid was used in stead of 1 0.2 g of 2-hydroxynaphthalene-3-carboxylic acid used in Example 1, and that no toning agent was added, 16.5 g of red pigment was obtained.

The toning effects were evaluated by means of the red pigments obtained in Examples 1–15 and in reference example 1, and the results are shown in table 1.

The toning effects were evaluated by means of the red pigments obtained in Examples 16–17 and in reference example 2, and the results are shown in table 2.

The color tone of the pigment powder was visually evaluated by means of Macbeth Spectra Light SPL-75 (Gretag Macbeth Co.) with daylight lamp. The color tones of the examples 1–15 were evaluated by comparison with that of the reference example 1 as a standard tone, and examples 16–17 were compared with that of the reference example 2.

Excitation purity (Pe) and brightness (Y) of the respective pigment powder was measured by means of Color Meter ZE2000 (Nihon Denshoku Co.) according to Japanese Industrial Standard (JIS) Z8701.

TABLE 1

|  | toning agent (mol %) | p e (%) | Y (%) | color tone |
|---|---|---|---|---|
| example 1 | 2.0 | 88.9 | 7.20 | bluish |
| example 2 | 2.0 | 88.6 | 6.74 | bluish |
| example 3 | 2.0 | 89.1 | 7.56 | bluish |
| example 4 | 2.0 | 88.6 | 7.60 | moderately bluish |
| example 5 | 2.0 | 87.9 | 7.55 | moderately bluish |
| example 6 | 2.0 | 85.9 | 6.75 | slightly bluish |
| example 7 | 2.0 | 85.7 | 7.90 | slightly bluish |
| example 8 | 2.0 | 85.1 | 7.84 | slightly yellowish |
| example 9 | 2.0 | 84.7 | 7.90 | slightly yellowish |
| example 10 | 2.0 | 85.0 | 8.13 | slightly yellowish |
| example 11 | 2.0 | 84.5 | 7.27 | moderately yellowish |
| example 12 | 2.0 | 83.4 | 8.76 | moderately yellowish |
| example 13 | 2.0 | 85.4 | 8.06 | moderately yellowish |
| example 14 | 2.0 | 84.2 | 9.32 | yellowish |
| example 15 | 2.0 | 86.8 | 9.05 | slightly yellowish |
| ref. 1 | none | 85.6 | 8.02 | standard |

TABLE 2

|  | toning agent (mol %) | p e (%) | Y (%) | color tone |
|---|---|---|---|---|
| example 16 | 2.0 | 80.7 | 7.77 | moderately yellowish |
| example 17 | 2.0 | 84.1 | 6.95 | moderately bluish |
| ref. 2 | none | 81.4 | 7.06 | standard |

EXAMPLES 18–20

According to the same manner as described in Example 1 with the exception that the amount of the toning agent, 2-hydroxy-3-methoxycarbonyl-6-carboxynaphthalene to the whole amount of the mixed coupler composition was changed to 5, 8, and 10 mol % respectively, to provide red pigments of the examples were obtained.

Comparative Examples 1–4

Red pigment A was obtained according to the same manner as described in Example 1 with the exception that the whole coupler composition used in the example was replaced with a sole coupler component, 2-hydroxy-3-methoxycarbonyl-6-carboxynaphthalene.

The pigment obtained in reference example 1 (obtained by using 2-hydroxynaphthalene-3-carboxylic acid as sole coupler component) and the pigment A were blended to give the mole ratio between the couplers being 98:2, 95:2, 92:8 and 90:10.

Excitation purity and color tone of the red pigments obtained in Examples 1, 18–20 and Comparative examples 1–4 are shown in table 3. Table 3 illustrate the difference between the pigments obtained by admixing the toning agent with the primary coupler component followed by diazotization, and those obtained by mixing two azo pigments obtained by diazotizing with the coupler component and the toning agent respectively.

TABLE 3

|  | toning agent (mol %) | Pe(%) | color tone |
|---|---|---|---|
| example 1 | 2.0 | 88.9 | bluish |
| example 18 | 5.0 | 86.7 | bluish |
| example 19 | 8.0 | 84.5 | slightly dark bluish |
| example 20 | 10.0 | 83.9 | moderately dark bluish |
| comp.ex. 1 | 2.0 | 85.6 | slightly bluish |
| comp.ex. 2 | 5.0 | 85.0 | moderately bluish |
| comp.ex. 3 | 8.0 | 84.3 | bluish |
| comp.ex. 4 | 10.0 | 83.1 | bluish |
| ref. 1 | none | 85.6 | standard |

The relationship between the amount of the toning agent in the mixed coupler composition and the excitation purity, in respect of the red pigments obtained in Examples 18–20 and Comparative examples 1–4.

INDUSTRIAL APPLICABILITY

According to the process of this invention, differently toned azo pigments to meet a wide variety of requirements in relation to coloring can be provided, and therefore the present invention is highly valuable from an industrial point of view.

What is claimed is:

1. A mixed coupler composition consisting essentially of:
   a) a hydroxynaphthalene monocarboxylic acid or a derivative thereof, and
   b) a compound having the formula [1]:

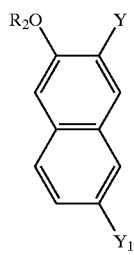

(I)

wherein
   Y is —(CONH)n-X or —COR,
   $Y^1$ is —(CONH)n-$X^1$ or —$COR^1$,
   wherein X and $X^1$ are optionally branched alkyl groups having 1–20 carbon atoms, optionally substituted aromatic groups, or optionally substituted heterocyclic groups having conjugated double bonds,
   n is an integer of 1 or 2,
   R and $R^1$ are hydroxy groups, optionally branched alkoxy groups having 1–6 carbon atoms, benzyloxy groups, phenyloxy groups or phenacyloxy groups, provided that when either R or $R^1$ is a hydroxy group, said group may optionally form an acceptable salt,
   $R_2$ is a hydrogen atom, an optionally branched alkyl group having 1–6 carbon atoms, an acyl group having 1–6 carbon atoms or a phenyl alkyl group.

2. The mixed coupler composition of claim 1 wherein the total amount of the compounds of formula (I) is less than 1 mol % of the total amount of the mixed coupler composition.

3. The mixed coupler composition of claim 1, wherein the hydroxynaphthalene monocarboxylic acid is 2-hydroxynaphthalene-3-carboxylic acid or 2-hydroxynaphthalene-6-carboxylic acid.

4. A process for preparing an azo pigment comprising the step of coupling the mixed coupler composition of claim 1 and a diazonium salt of an aromatic compound.

5. A mixed coupler composition comprising:
   a) a hydroxynaphthalene monocarboxylic acid or a derivative thereof, and
   b) a compound having the formula [1]:

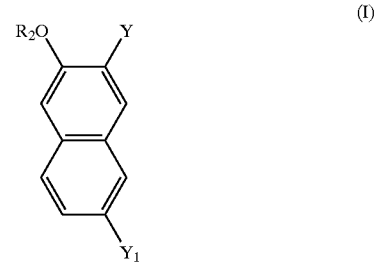

(I)

wherein
   Y is —(CONH)n-X or —COR,
   $Y^1$ is —(CONH)n-$X^1$ or —$COR^1$,
   wherein X and $X^1$ are optionally branched alkyl groups having 1–20 carbon atoms, optionally substituted aromatic groups, or optionally substituted heterocyclic groups having conjugated double bonds,
   n is an integer of 1 or 2,
   R and $R^1$ are hydroxy groups, optionally branched alkoxy groups having 1–6 carbon atoms, benzyloxy groups, phenyloxy groups or phenacyloxy groups, provided that when either R or $R^1$ is a hydroxy group, said group may optionally form an acceptable salt,
   $R_2$ is a hydrogen atom, an optionally branched alkyl group having 1–6 carbon atoms, an acyl group having 1–6 carbon atoms or a phenyl alkyl group.

6. An azo pigment obtained by the process of claim 4 with a modified tone.

* * * * *